United States Patent
Weber et al.

(10) Patent No.: US 7,713,221 B1
(45) Date of Patent: May 11, 2010

(54) STRAP TENSIONING OF ORTHOPEDIC APPLIANCES

(75) Inventors: James J. Weber, Santa Barbara, CA (US); John P. Hely, Roanoke, TX (US)

(73) Assignee: Weber Orthopedic Inc., Santa Paula, CA (US)

( * ) Notice: Subject to any disclaimer, the term of this patent is extended or adjusted under 35 U.S.C. 154(b) by 166 days.

(21) Appl. No.: 11/642,435

(22) Filed: Dec. 21, 2006

(51) Int. Cl.
*A61F 5/00* (2006.01)
*A61B 17/00* (2006.01)
*A61F 5/28* (2006.01)

(52) U.S. Cl. .................. 602/5; 606/201; 128/99.1
(58) Field of Classification Search .............. 602/5, 602/20, 21, 75; 24/16, 32, 306, 442, 198; 2/338; 606/203, 201; 128/95.1, 99.1, 100.1, 128/101.1, 105.1, 877, 878
See application file for complete search history.

(56) References Cited

U.S. PATENT DOCUMENTS

| | | | | |
|---|---|---|---|---|
| 1,601,173 | A | | 9/1926 | Hill |
| 1,723,841 | A | * | 8/1929 | Butler .................. 24/198 |
| 3,112,496 | A | | 12/1963 | Dritz |
| 3,640,273 | A | | 2/1972 | Ray |
| 3,747,171 | A | | 7/1973 | Montague |
| 3,786,804 | A | | 1/1974 | Lewis |
| 4,149,540 | A | * | 4/1979 | Hasslinger ............... 606/203 |
| 4,472,839 | A | | 9/1984 | Johansen |
| 4,527,289 | A | | 7/1985 | Shea |
| 4,878,274 | A | * | 11/1989 | Patricy ................... 24/306 |
| 4,917,049 | A | | 4/1990 | Peterson |
| 5,036,864 | A | | 8/1991 | Yewer, Jr. |
| 5,201,100 | A | * | 4/1993 | Cardinale ................ 24/306 |
| 5,203,053 | A | * | 4/1993 | Rudd ..................... 24/306 |
| 5,309,575 | A | | 5/1994 | Lookhoof |
| 5,500,959 | A | | 3/1996 | Yewer, Jr. |
| 5,548,871 | A | * | 8/1996 | Trethewey .............. 24/16 R |
| D422,709 | S | | 4/2000 | Caswell |
| 6,117,098 | A | * | 9/2000 | Weber et al. ............. 602/27 |
| 6,131,249 | A | * | 10/2000 | Suenaga ................. 24/306 |
| 2007/0250109 | A1 | * | 10/2007 | Kerstein et al. .......... 606/203 |

* cited by examiner

*Primary Examiner*—Patricia M Bianco
*Assistant Examiner*—Victoria Hicks
(74) *Attorney, Agent, or Firm*—William W. Haefliger

(57) ABSTRACT

A tightener for orthopedic use, includes a guide loop having opposite sections, a first orthopedic strap anchored to one section for passing about a user's arm, leg or like member, and then passage through the loop to extend in a first tightening direction, a second orthopedic strap anchored to another loop section to extend in a second and opposite tightening direction, whereby the two straps extending in the first and second directions can be manually pulled in those directions to tighten the first strap about the member, and two tensioned straps can then be connected by push together connection to tightened extents of the first strap to hold tension transmission via the loop sections and straps.

10 Claims, 2 Drawing Sheets

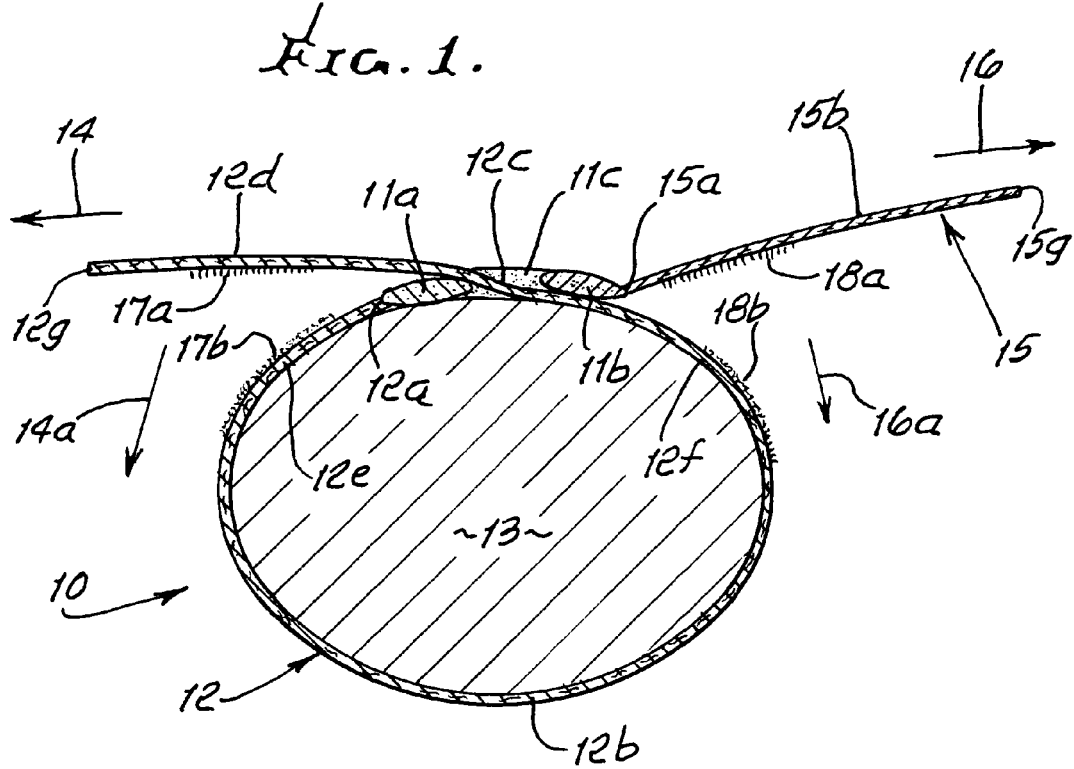
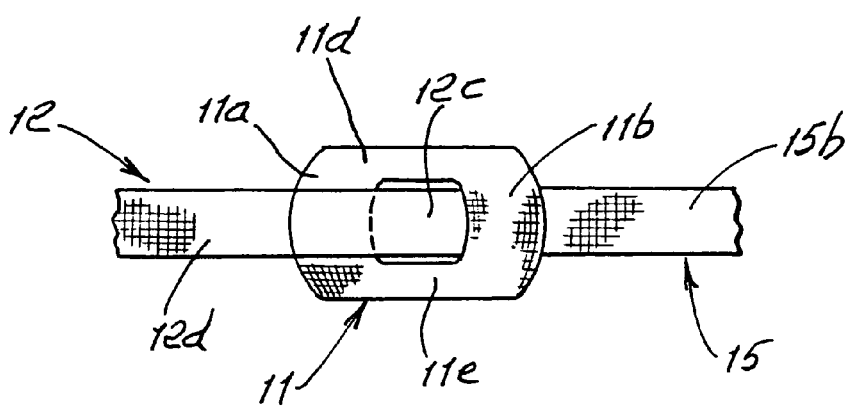

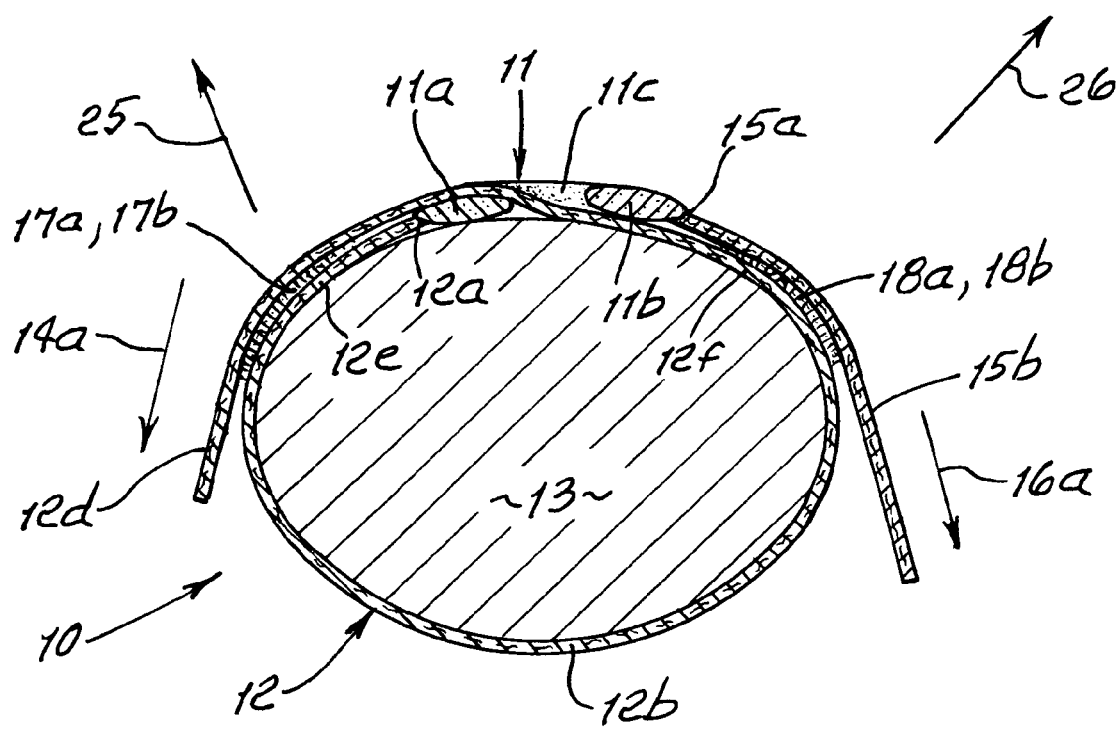

STRAP TENSIONING OF ORTHOPEDIC APPLIANCES

BACKGROUND OF THE INVENTION

This invention relates generally to orthopedic appliances that are placed in tension about the arm, leg, or other body member; and more particularly to a greatly improved such appliance facilitating rapid tensioning of wrap-around strap structures and associated interconnection of tensioned strap section, all by sequential and multidimensional manipulating of strap end portions.

There is continuing need for orthopedic appliances that facilitate rapid and accurate wrap-around connection of strap structures to the arm, leg, or other body member. There is also need for such appliances which enable rapid disconnection of the strap structure from tensioned wrap-around condition. There is, in addition, need for the particular appliance as disclosed herein, operating as described and providing greatly improved results, as will appear.

SUMMARY OF THE INVENTION

It is a major object of the invention to provide an improved, simple and efficient tensioning appliance, meeting the above needs. Basically, the device enables manual manipulation of strap end portions to adjustably tension the appliance in wrapped condition; to establish interconnection of strap extents by application of strap transmitted push together forces to said strap extents; and to facilitate disconnection of such strap extents by application of pull-apart force (for example pull-up force) to two oppositely extending strap end portions.

It is another object of the invention to provide for tensioning as via pulling of two oppositely extending strap extents and for guiding such pulling as by provision of a loop to which two straps are operatively attached, one of the straps passing through the loop.

It is a further object of the invention to provide for releasable interconnection of tensioning strap extents as by guided push-together operative attachment of tensioned strap extents, in a rapid and efficient manner as will appear. Such operation attachment is typically established proximate the loop to which two straps are operatively attached.

Yet another object is to provide a stiff, strap guide loop to withstand opposite direction tensioning of tightening straps, without substantial endwise deflection; while maintaining the straps oriented in general alignment proximate the loop to prevent tensioning misalignment, all without need for buckle or retention structures within the loop bounded area.

An added object is to provide for strap positioning characterized in that endwise tension on strap end portions is established and maintained, while forcible face to face operative connection of strap extents is simultaneously established at two endwise spaced locations.

These and other objects and advantages of the invention, as well as the details of an illustrative embodiment, will be more fully understood from the following specification and drawings, in which:

DRAWING DESCRIPTION

FIG. 1 is a side elevation showing use of the tightener of the invention;

FIG. 2 is a view like FIG. 1 showing the tightener after completion of tightening and after establishment of a tightened condition; and FIG. 3 is a top plan view of the tightener as seen in FIG. 2.

DETAILED DESCRIPTION

Referring first to FIG. 1, the preferred tightener 10 comprises a) a stiff loop 11 having opposite stiff, or rigid, sections 11a and 11b, which, as shown, have elongated oval cross sections, b) a first orthopedic flexible strap 12 anchored at 12a to one of the loop sections, such as section 11a, for passing of the strap as at 12b about a user's arm, leg or like member 13, and then passage, as at 12c through the loop opening 11c to extend at 12d in a first tightening direction 14, c) a second orthopedic flexible strap 15 anchored, as at 15a to another of the loop sections, such as section 11b, to extend at 15b in a second and opposite tightening direction 16;

d) whereby the two straps 12 and 15 extending in directions 14 and 16 can be manually pulled in those directions to tighten the first strap at 12b about the member 13, e) and the two tensioned straps (or strap extents or portions 12d and 15b) can then be anchored (or removably connected by push together connection) to tightened extents 12e and 12f of the first strap facing 12d and 15b, respectively, thereby to hold tension transmission via the loop sections and straps.

Non-stiffness of sections 11a and 11b leads to their flexing when tensioned by the straps, and preventing of a selected tensioned location.

As will be understood, the push together connections are typically established at four spaced locations on the straps while the user's hands maintain strap tension, as by pull down of the tensioned end extents of the straps. Thus, two locations are mutually at facing extents of strap portions 12d and 12e, and at facing extents of strap portions 15b and 12f. Strap portions 12d and 12e are associated with tensioning direction 14; and strap portions 15b and 12f are associated with direction 16. Note that strap portions 12e and 12f are typically angled downwardly, when tightened, so that pull down of tensioned sections 12d and 15b effects the connections. See FIG. 2, and arrows 14a and 16a.

In this regard, and preferably, hook and pile material such as VELCRO is provided on strap extents for push together downward anchoring of the strap extents after left and right tightening, as described. An easily established pulling of the strap extents, and then pushing together the pulled extents, is thereby realized. See for example interconnectible hook and pile material at 17a and 17b, and interconnectible hook and pile material at 18a and 18b.

FIG. 3 shows two loop stretches 11d and 11e extending generally in longitudinal directions, generally the same as directions 14 and 16, for transmitting tension between pulled sections 11a and 11b.

A further feature is the provision of strap terminals 12g and 15g spaced sufficiently from the loop 11, and loop pulled sections 11a and 11b, to enable manual grasping and pulling oppositely of the two end portions of the straps 12 and 15, in directions 14 and 16, for tightening, as described, and also for loosening of the appliance or device, as by upward pulling of the strap end sections in directions 25 and 26 seen in FIG. 2.

One method of use of the appliance or device includes the straps f) wrapping of the straps about the user's arm, leg, or other member;

g) passing of one strap through the loop and orienting the strap end portions to extend oppositely as in directions 14 and 16;

h) tensioning of the strap end portions that extend in direction 14 and 16;

i) deflecting the strap and portions toward one another, while maintaining strap endwise tensioning as at the described two VELCRO locations, to establish their interconnections at the described two VELCRO locations, for holding the appliance to the arm, leg or other member;

j) and ultimate loosening of the appliance as by upward pulling of the strap end portions to disconnect the VELCO anchors.

In this regard, it will be further noted that the guide loop is sufficiently stiff to withstand opposite directional tensioning of the tightener straps, without substantial loop endwise deflection, while maintaining the straps oriented in general alignment proximate the loop to prevent tensioning misalignment. Also, the loop defines a bounded area free of any retention structure other than the strap passing therethrough.

We claim:

1. A tightener for orthopedic use, comprising in combination
   a) a guide loop having opposite primary and secondary non-metallic sections, said sections having cross sections which have elongated oval layer shape,
   b) a first orthopedic strap anchored to said primary section for passing about a user's arm, or leg member, and then passage through the loop to extend in a first tightening direction, by passing generally linearly under the oval surface of the secondary section and then over the oval surface of the primary section, the strap being in contact with said oval surfaces and extending in substantially same linear direction as directed by such dual contacts,
   c) a second orthopedic strap anchored to said secondary section to extend in a second and opposite tightening direction,
   d) whereby the two straps extending in said first and second directions can be manually pulled in said opposite directions to tighten the first strap about said member,
   e) and the two tightened orthopedic straps then connected by push together connection to tightened extent of the first strap to hold tension transmission via said loop sections and straps,
   f) each of said primary and secondary, elongated oval cross section layer shaped sections having inward and outward facing sides, said first strap extending directly adjacent and flatly engaging a substantially flat surface of said inward facing side of said secondary section and also extending directly adjacent and flatly engaging a substantially flat surface of said outward facing extent of said primary section, the straps having terminals attached only to edges of the sections.

2. The combination of claim 1 wherein said push together connections are at four spaced locations on said straps.

3. The combination of claim 2 wherein two of said spaced location are associated with said first direction, and a second two of said spaced locations are associated with said second direction.

4. The combination of claim 3 wherein hook and pile material is on said tightened extent of the first strap.

5. The combination of claim 3 wherein hook and/or pile material is located at said first two locations, and hook and/or pile material is also located at the second of said locations.

6. The combination of claim 1 wherein the guide loop is sufficiently stiff to withstand opposite directional tensioning of the tightener straps, without substantial loop endwise deflection, while maintaining the straps oriented in general alignment proximate the loop to prevent tensioning misalignment.

7. The combination of claim 6 wherein the loop defines a bounded area free of any retention structure other than the strap passing therethrough.

8. The combination of claim 1 where the loop has stretches that are tensioned during said tension transmission via the loop sections.

9. The combination of claim 1 wherein the first and second straps have terminals spaced from said loop to enable manual grasping and pulling of the two straps in said directions for tightening and loosening of the tensioned device.

10. The combination of claim 1 wherein the straps have positions characterized in that endwise tensioning of strap end portions is established and maintained while forcible face to face operative connection of strap extents is simultaneously established at two endwise spaced locations.

* * * * *